United States Patent [19]

Fourtillan et al.

[11] Patent Number: 5,763,471

[45] Date of Patent: Jun. 9, 1998

[54] MELATONINERGIC AGONIST SPIRO [INDOLEPYRROLIDINE] DERIVATIVES, PROCESS FOR THEIR PREPARATION AND THEIR USE AS MEDICINAL PRODUCTS

[75] Inventors: Jean-Bernard Fourtillan; Marianne Fourtillan, both of Migne-Auxances; Jean-Claude Jacquesy, Buxerolles; Marie-Paule Jouannetaud, Poitiers; Bruno Violeau, Marcay; Omar Karam, Poitiers, all of France

[73] Assignees: CEMAF; Laboratories Besins Iscovesco, both of France

[21] Appl. No.: 722,105

[22] PCT Filed: Apr. 6, 1995

[86] PCT No.: PCT/FR95/00443

§ 371 Date: Dec. 11, 1996

§ 102(e) Date: Dec. 11, 1996

[87] PCT Pub. No.: WO95/27712

PCT Pub. Date: Oct. 19, 1995

[30] Foreign Application Priority Data

| Apr. 7, 1994 | [FR] | France | 94 04102 |
| Sep. 2, 1994 | [FR] | France | 94 10558 |

[51] Int. Cl.$^6$ ........................... A61K 31/40
[52] U.S. Cl. .................. 514/409; 548/409; 548/410
[58] Field of Search ............... 514/409; 548/409, 548/410; 424/401

[56] References Cited

U.S. PATENT DOCUMENTS

| 4,233,307 | 11/1980 | Ono et al. | 424/267 |
| 5,093,352 | 3/1992 | Dubocovich | 514/419 |
| 5,196,435 | 3/1993 | Clemens et al. | 514/284 |
| 5,283,343 | 2/1994 | Dubocovich et al. | 548/496 |

FOREIGN PATENT DOCUMENTS

| 0 513 702A2 | 11/1992 | European Pat. Off. |
| 0 549 916A2 | 7/1993 | European Pat. Off. |
| 26 45 865 | 5/1977 | Germany |
| WO A 8901472 | 2/1989 | WIPO |

OTHER PUBLICATIONS

I.M. Young et al., "The mass spectrometric analysis of the urinary metabolites of melatonin", Chemical Abstracts, vol. 103, Abstract No. 135700, 1985.

M. Ikeda et al., "Reactions of Tryptophols and N-acetyltryptamines With Iodine Azide Formation . . ." *J. Chemical Society, Perkin Transactions 1*, pp. 3061–3063 (1979).

P. Garratt et al., "Mapping the Melatonin Receptor. 3. Design and Synthesis of Melatonin Agonists and Antagonists Derived from 2-Phenyltryptamines". *J. Med. Chem.*, vol. 38. No. 7. pp. 1132–1139 (1995).

P. Garratt et al., "Mapping the Melatonin Receptor 1. the 5-Methoxyl Group Of Melatonin Is Not An Essential Requirement for Biological Activity", *Bioorganic and Medicinal Chemistry Letters*, vol. 4, No. 13, pp. 1555–1558 (1995).

K. Biswas et al., "Electrophilic Substitution in Indoles. Part 18 Cyclisation of N–Acyltryptamines", *J. Chem. Society, Perkin Transactions 1*, pp. 461–467 (1992).

J. Blau et al., "Mass Spectrometric and Nuclear Magnetic Resonance Confirmation of a 3,3–Spirocyclic Indole Derivative Formed From Melatonin and Related Acyl Tryptamines", Chemical Abstracts, vol. 88, No. 19, Abstract No. 136439z (1978).

J. M. Rosenfeld et al., "Use of Impregnated Reagents In the Pentafluorobenzylation of Indoleamine Metabolites", Chemical Abstracts, vol. 103, No. 9, Abstract No. 67829r (1985).

*Primary Examiner*—Joseph K. McKane
*Attorney, Agent, or Firm*—Finnegan, Henderson, Farabow, Garrett & Dunner, L.L.P.

[57] ABSTRACT

The present invention relates to spiro[3H-indole-3(2H),3'-pyrrolidine] derivatives of general formula I

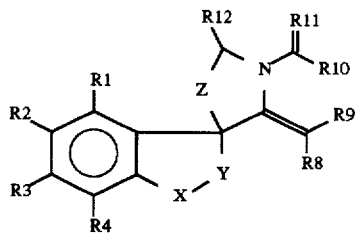

as defined in the description.

The invention also relates to a process for their preparation and to their therapeutic use, in particular for the treatment of complaints associated with melatonin disorders, and to the pharmaceutical and cosmetic compositions comprising them.

14 Claims, No Drawings

MELATONINERGIC AGONIST SPIRO [INDOLEPYRROLIDINE] DERIVATIVES, PROCESS FOR THEIR PREPARATION AND THEIR USE AS MEDICINAL PRODUCTS

This application is a 371 of PCT/FR95/00443 filed Apr. 6, 1995, published as WO95/27712 Oct. 19, 1995.

The present invention relates to novel melatoninergic agonist spiro[indolepyrrolidine] derivatives, to a process for their preparation and to their use as medicinal products.

Melatonin, N-acetyl-5-methoxytryptamine, is a pineal gland hormone, isolated by Lerner et al. (J. Am. Chem. Soc., 80, 1958, 2587) which has been the subject of many studies for its circadian activity, in the rhythm of sleep, for its effects on the production of testosterone, for its activity on the hypothalamus and in psychiatric disorders.

It has thus been envisaged to use melatonin and analogues thereof especially for the treatment of depression and psychiatric disorders, in particular stress, anxiety, depression, insomnia, schizophrenia, psychosis and epilepsy, and also for the treatment of sleep disorders associated with journeys ("jet lag"), neurode-generative diseases of the central nervous system such as Parkinson's disease or Alzheimer's disease, for treating cancers, or alternatively as a contraceptive or as an analgesic.

However, the direct use of melatonin in vivo has not proved to be very satisfactory, given that the first passage through the liver extracts more than 90% of the active principle.

Various melatonin analogues have been described, demonstrating two research routes which relate either to melatonin substituents (WO-A-89/01472, U.S. Pat. No. 5,283,343, U.S. Pat. No. 5,093,352 or WO-A-93/11761) or to the aromatic ring by replacing the indolyl group by a naphthyl group (FR-A-2 658 818, FR-A-2 689 124).

The present patent application proposes a novel route for the development of melatonin analogues having improved activity.

The present invention thus relates to novel spiro [indolepyrrolidine] derivatives of general formula

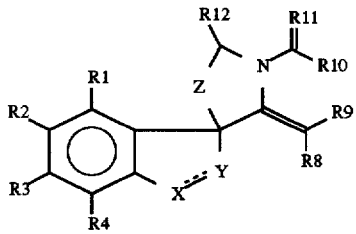

I in which

—X=Y— represents a divalent radical selected from

—NR5—CR6R7— (Ia)

or

—NR5—C— (Ib)
  $\|$
  R13 or

—N=CR14— (Ic)

Z represents an alkylene of formula —(CH$_2$)$_n$— with n equal to 1 or 2, preferably 1, R1, R2, R3 and R4 represent, independently of each other, a hydrogen atom, a hydroxyl radical or a lower alkyl, lower alkoxy, aryloxy, lower aralkoxy, halo or nitro radical, R5 represents a hydrogen atom or a lower alkyl, aryl, lower aralkyl, lower alkoxy, (lower)alkylcarbonyl or perhalo(lower)alkylcarbonyl radical, R6 and R7 represent, independently of each other, a hydrogen atom or a lower alkyl, aryl, lower aralkyl, lower alkoxy, (lower)alkylcarbonyl, perhalo(lower) alkylcarbonyl, (lower)alkylcarbonyloxy, perhalo (lower)alkylcarbonyloxy or halo radical, R8 and R9 represent, independently of each other, a hydrogen atom or a lower alkyl, aryl or lower aralkyl radical, R10 represents a hydrogen atom or a lower alkyl, aryl or lower aralkyl radical, each optionally being substituted with one or more halogens, a perhalo(lower)alkyl radical, an amino, (lower)alkylamino or (lower) dialkylamino radical, or a lower alkoxy radical, R11 represents an oxygen atom, a sulphur atom or a radical N—R15, R12 represents a hydrogen- atom or a lower alkyl radical, R13 represents an oxygen atom, a sulphur atom, a radical N—R16 or a substituted or unsubstituted methylene radical, R14 represents a hydrogen atom or a lower alkyl, lower alkoxy, lower alkylthio, aryl or lower aralkyl radical, R15 and R16 represent, independently of each other, a hydrogen atom or a lower alkyl radical, it being possible for R1—R2, R2–R3 and R3–R4 to form part of another ring, which may or may not be aromatic and may or may not contain a hetero atom, it being possible for R9 and R10 together to form an alkylene radical, preferably a methylene radical, which is optionally substituted, the racemic mixtures thereof, pure enantiomers thereof or the mixtures thereof in all proportions, and the therapeutically acceptable salts thereof.

The terms lower alkyl, lower alkoxy and perhalo(lower) alkyl refer generally to radicals in which the alkyl residue comprises between 1 and 6 carbon atoms.

These are preferably linear or branched C$_1$–C$_4$ alkyl residues, chosen more particularly from the methyl, ethyl, n-propyl, i-propyl, n-butyl, i-butyl and t-butyl groups.

The term aryl generally denotes aromatic and heteroaromatic groups, in particular aryls chosen from the phenyl, thienyl, furyl, pyridyl and naphthyl groups.

The aryl radicals may also be substituted with one or more substituents chosen in particular from the halo, lower alkoxy and lower alkyl radicals defined above.

The term lower aralkyl will be understood to refer to the combination of a lower alkyl and an aryl as defined above. This will preferably be the benzyl radical, which is optionally substituted.

The halo radicals are preferably chosen from fluorine, chlorine, bromine and iodine atoms.

The perhalo radicals are preferably perfluoro radicals.

When R1–R2, R2–R3 and R3–R4 form part of another ring, which is aromatic, with or without a hetero atom, this is preferably another benzenic ring, which is optionally substituted, or a pyridyl ring, which is optionally substituted.

When R1–R2, R2–R3 and R3–R4 form part of another non-aromatic ring, they together preferably form a divalent radical of formula —O—(CH$_2$)$_m$—, m being equal to 2 or 3, which is optionally substituted, or a divalent radical of formula —O—(CH$_2$)$_p$—O—, p being equal to 1 or 2, which is optionally substituted.

The derivatives according to the invention contain at least one asymmetric carbon of R or S configuration, the carbon at position 3 of the spiro ring being connected in all cases to 4 separate substituents.

The present invention thus relates to the racemic mixtures of the derivatives of general formula I, as well as to the pure enantiomers thereof, or to the mixtures thereof in all proportions.

The therapeutically acceptable salts of the derivatives according to the invention are the usual organic or inorganic salts of the art, in particular the hydrochlorides, tosylates, mesylates and citrates, as well as the solvates such as the hydrates or hemihydrates of the compounds of general formula I.

The present invention relates more particularly to the derivatives of general formula I for which n is equal to 1.

R11 preferably represents an oxygen atom and R8 and R9 preferably represent a hydrogen atom.

Advantageously, at least one of the substituents R2 and R3 is other than a hydrogen atom and preferably represents a hydroxyl or lower alkoxy radical, in particular a methoxy radical.

In a preferred manner, R1, R4 and R6 represent a hydrogen atom.

Among the preferred derivatives according to the invention, R12 represents a hydrogen atom and R10 is advantageously a lower alkyl radical, preferably a methyl, an ethyl, an n-propyl or a perfluoromethyl, perfluoroethyl or perfluoropropyl radical, preferably a perfluoroethyl radical.

The present invention also relates to the process for the preparation of the derivatives of general formula I as defined above.

The derivatives of general formula I, for which —X=Y— represents a divalent radical of formula Ia, are obtained by reduction of the corresponding derivative of formula Ic according to the usual techniques, such as, for example, with a metal hydride, in order to give the derivative of formula Ia for which R5 represents a hydrogen atom, and are then transformed, where appropriate, so as to introduce the substituent R5 which is other than a hydrogen atom, according to the usual methods for condensation with an amine.

In the particular case where R11 represents an oxygen atom, R10 represents a perhalo(lower)alkyl (—R20) radical, R5 represents a perhalo(lower)alkylcarbonyl (—CO—R20) radical, R6 represents a hydrogen atom and R7 represents a perhalo(lower)alkylcarbonyloxy (—O—CO—R20) radical, the derivatives of formula Ia may be obtained directly by reacting the compound of general formula IIa

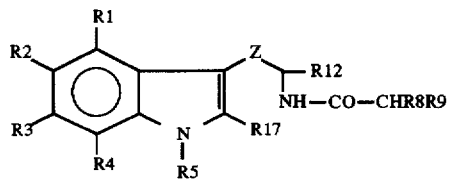

for which R1, R2, R3, R4, R5, R8, R9, R12 and Z are defined above and R17 represents a hydrogen atom, with an excess of anhydride of formula III

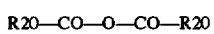

R20—CO—O—CO—R20    III in which R20 represents a perhalo(lower)alkyl residue.

The derivatives of general formula I, for which —X=Y— represents a divalent radical of formula Ib, R11 represents an oxygen atom and R10 represents a perhalo (lower)alkyl (—R20) radical, are obtained by reacting a derivative of general formula IIa as defined above, and in which R17 represents a bromine atom, with an excess of anhydride of formula III defined above.

The derivative of general formula I'b

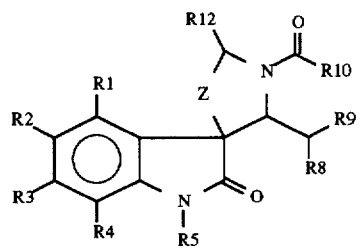

in which R10 represents a perhalo (lower) alkyl radical, is thus obtained.

In order to obtain the corresponding derivatives for which R10 is other than a perhalo(lower)alkyl radical, "deprotection" of the spiroindole amine is thus carried out by reacting the derivative of general formula I'b obtained above with a base, preferably potassium carbonate, in a suitable solvent, for example methanol or a methanol/water mixture.

An intermediate of general formula IVa

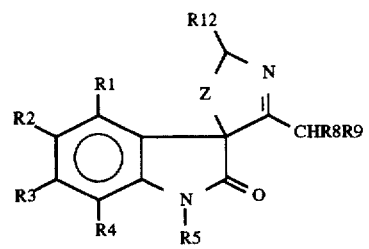

in which R1, R2, R3, R4, R5, R8, R9, R12 and Z are defined above, is thus obtained, followed by condensation of the radical R10—CO—, for which R10 is other than a perhalo (lower)alkyl radical, with the free amine according to the usual techniques for the preparation of amides, in particular the techniques of acid activation optionally with a coupling agent, such as those employed in peptide synthesis, or alternatively by reaction with the corresponding anhydride of formula R10—CO—O—CO—R10.

The derivatives of general formula I, for which —X=Y— represents a divalent radical of formula Ic, R11 represents an oxygen atom and R10 represents a perhalo (lower)alkyl (—R20) radical, are obtained by reacting a derivative of general formula IIb

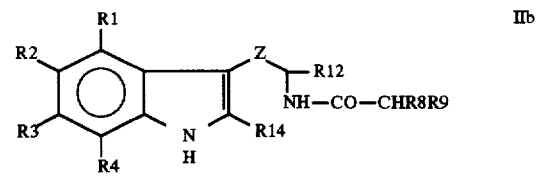

in which R1, R2, R3, R4, R8, R9, R12 and Z are defined above and R14 is other than a hydrogen atom, with an excess of anhydride of formula III defined above.

The derivative of formula I'c

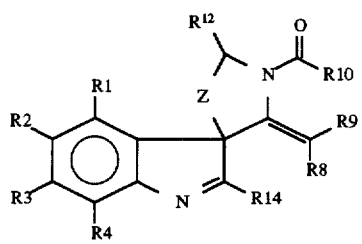

in which R1, R2, R3, R4, R8, R9, R12, R14 and Z are defined above and R10 represents a perhalo(lower)alkyl radical, is obtained.

In order to obtain the corresponding derivatives for which R10 is other than a perhalo(lower)alkyl radical, "deprotection" of the spiroindole amine is thus carried out by reacting the derivative of general formula I'c obtained above with a base, preferably potassium carbonate, in a suitable solvent, for example methanol or a methanol/water mixture.

An intermediate of general formula IVb

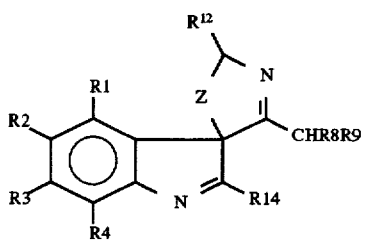

in which R1, R2, R3, R4, R8, R9, R12, R14 and Z are defined above, is thus obtained, followed by condensation of the radical R10—CO—, for which R10 is other than a perhalo(lower)alkyl radical, with the free amine according to the usual techniques for the preparation of amides, in particular the techniques of acid activation optionally with a coupling agent, such as those employed in peptide synthesis, or alternatively by reaction with the corresponding anhydride of formula R10—CO—O—CO—R10.

In order to obtain the specific derivatives of general formula Ic, for which R14 represents a lower alkoxy radical, the derivative of corresponding general formula I'b defined above is reacted with Meerwein's reagent's $(R21)_3OBF_4$ in solution in methylene chloride, where R21 represents a lower alkyl.

In order to obtain the derivatives of general formula I for which R11 and R13 are other than an oxygen atom and R14 is other than a lower alkoxy or a lower alkyl, the derivatives obtained above are thus converted into the corresponding derivatives, according to the usual techniques for the conversion of carbonyls.

The starting materials of formula II are commercially available, such as melatonin, or are described in particular in EP-A-0,527,687 and WO-A-89/01472, or may be prepared from these derivatives. The present invention also relates to the derivatives of formulae IIa and IIb, as defined above, with R17 representing a hydrogen atom or a bromine atom and R14 being other than a hydrogen atom, as products required for the preparation of the derivatives of general formula I according to the invention.

The invention also relates to the intermediates of formulae IVa and IVb as defined above, which are useful in particular for the preparation of the derivatives of general formula I, for which R10 is other than a perhalo(lower)alkyl radical.

The enantiomers of the derivatives of formula I and the mixtures thereof in all proportions may be obtained by the usual methods for the resolution of racemic mixtures, in particular by selective crystallization in the presence of a chiral acid.

The examples below for the preparation of derivatives according to the invention make it possible to illustrate the present invention without, however, seeking to limit the scope thereof.

Examples of derivatives of formula Ia according to the invention, for which R1, R3, R4, R6, R8, R9 and R12 represent a hydrogen atom, R11 represents an oxygen and n is equal to 1, are given in Table I below.

TABLE I

| Compound | R2 | R5 | R7 | R10 |
| --- | --- | --- | --- | --- |
| 1 | OCH$_3$ | CO—C$_2$F$_5$ | O—CO—C$_2$F$_5$ | C$_2$F$_5$ |
| 2 | OCH$_3$ | CO—F$_3$ | O—CO—CF$_3$ | CF$_3$ |
| 28 | H | H | Et | CH$_3$ |

Examples of derivatives of formula Ib according to the invention, for which R4, R8, R9 and R12 represent a hydrogen atom, R13 and R11 represent an oxygen and n is equal to 1, are given in Table II below.

TABLE II

| Compound | R1 | R2 | R3 | R5 | R10 |
| --- | --- | --- | --- | --- | --- |
| 3 | H | OCH$_3$ | H | H | C$_2$F$_5$ |
| 4 | H | OCH$_3$ | H | H | CF$_3$ |
| 6 | H | OCH$_3$ | H | H | CH$_3$ |
| 7 | H | OCH$_3$ | H | H | C$_2$H$_5$ |
| 8 | H | OCH$_3$ | H | H | C$_3$H$_7$ |
| 9 | Br | OCH$_3$ | H | H | C$_2$F$_5$ |
| 10 | H | OCH$_3$ | Br | H | C$_2$F$_5$ |
| 11 | Br | OCH$_3$ | H | H | CH$_3$ |
| 12 | H | OCH$_3$ | Br | H | C$_2$H$_3$ |
| 13 | H | OCH$_3$ | H | CH$_3$ | C$_2$F$_5$ |
| 15 | H | OCH$_3$ | H | CH$_3$ | CH$_3$ |
| 22 | H | H | H | H | C$_2$F$_5$ |
| 24 | H | H | H | H | CH$_3$ |

Examples of derivatives of formula Ic according to the invention, for which R1, R3, R4, R8, R9 and R12 represent a hydrogen atom, R11 represents an oxygen and n is equal to 1, are given in Table III below.

TABLE III

| Compound | R2 | R16 | R10 |
| --- | --- | --- | --- |
| 16 | OCH$_3$ | OC$_2$H$_5$ | CF$_3$ |
| 18 | OCH$_3$ | OC$_2$H$_5$ | CH$_3$ |
| 19 | OCH$_3$ | C$_2$H$_5$ | C$_2$F$_5$ |
| 21 | OCH$_3$ | C$_2$H$_5$ | CH$_3$ |
| 25 | OCH$_3$ | C$_2$H$_5$ | C$_2$F$_5$ |
| 27 | OCH$_3$ | C$_2$H$_5$ | CH$_3$ |

The synthesis of the products of general formula I, presented in Tables I to III above, is given in detail below.

STARTING MATERIALS

2-Bromomelatonin

Melatonin (1.18 g) is dissolved in 100 ml of THF in a 250 ml round-bottomed flask and one equivalent of phenyltrimethylammonium tribromide is then added (pyridinium tribromide may also be used). The mixture is stirred under nitrogen for 30 min.

The THF is evaporated off under reduced pressure. The crude product is diluted with water and then extracted with dichloromethane. The bromomelatonin is obtained after flash chromatography on silica (eluent: ethyl acetate dried over magnesium sulphate). Yield=74%

Formula: $C_{13}H_{15}N_2O_2Br$ M=311.17 NMR: $^1H$ (CD$_3$COCD$_3$) 1.87 (5, 3H, CH$_3$ acetyl), 2.86 (t, 2H, CH$_2$), 3.42 (q, 2H, CH$_2$—N), 3.81 (s, 3H, OC$\underline{H}_3$), 6.77 (dd, 1H, H-6), 7.14 (d, 1H, H-4), 7.23 (d, 1H, H-7), 7.2 (broad s, 1H, H—N amide), 10.51 (broad s, 1H, H—N indole)

2,4-Dibromomelatonin and 2,6-dibromomelatonin

By following the above procedure with 2-bromomelatonin as starting material, the mixture of 2,4- and 2,6-dibromomelatonin is obtained.

1-Methylmelatonin

Melatonin (600 mg) is dissolved in DMSO (2 ml) in a 25 ml round-bottomed flask, and potassium hydroxide (6 pellets~300 mg) is then added. After stirring for 15 minutes, methyl iodide (0.6 ml) is added. The mixture is stirred overnight, diluted with water and then acidified with 2N hydrochloric acid. After extraction (dichloromethane 3 times), washing with acidic water, drying over magnesium sulphate and evaporation of the solvent, 1-methylmelatonin is obtained quantitatively.

Formula: $C_{14}H_{18}N_2O_2$ M=246.30 g·mol$^{-1}$, NMR: $^1H$ (CD$_3$COCD$_3$): 1.88 (s, 3H, CH$_3$ acetyl), 2.92 (t, 2H, CH$_2$), 3.45 (q, 2H, CH$_2$—N), 3.6 (8, 3H, CH$_3$—N), 3.78 (8, 3H, OC$\underline{H}_3$), 6.5 (broad s, 1H, H—N amide), 6.77 (s, 1H, H-2), 6.86 (d, 1H, H-6), 7.01 (s, 1H, H-4), 7.08 (d, 1H, H-7).

1-Methyl-2-broiomelatonin

A procedure identical to the preparation of 2-bromomelatonin is followed, with 1-methylmelatonin as the starting material.

Formula: $C_{14}H_{17}N_2O_2Br$ M=325.20 g·mol$^{-1}$ NMR: $^1H$ (CD$_3$COCD$_3$): 1.90 (s, 3H, CH$_3$ acetyl), 2.92 (t, 2H, CH$_2$), 3.45 (q, 2H, CH$_2$—N), 3.67 (s, 3H, CH$_3$—N), 3.8 (s, 3H, OC$\underline{H}_3$), 5.96 (broad s, 1H, H—N amide), 6.85 (d, 1H, H-6), 6.97 (s, 1H, H-4), 7.12 (d, 1H, H-7).

2-Ethylmelatonin

6-Methoxyharmalan (620 mg) is dissolved in ethylene glycol (17 ml), followed by addition of potassium hydroxide (1.5 g) and hydrazine (0.73 ml). The mixture is maintained at reflux for 2 hours. The medium is then diluted with water and extracted with ether (3 times). The organic phase is treated with 6N hydrochloric acid (three times). The aqueous phase recovered is basified with 20% potassium hydroxide solution and then extracted with ethyl acetate. After evaporation, 2-ethyl-5-methoxytryptamine is recovered (69%).

The latter product (420 mg) is then acetylated in pyridine (1.2 ml) in the presence of acetic anhydride (1 ml). After removal of the pyridine (vacuum suction), the crude product is taken up in water and extracted with ethyl acetate. After evaporation, 2-ethylmelatonin is recovered (75%).

Formula: $C_{15}H_{20}N_2O_2$ M=260.33 g·mol$^{-1}$ NMR: $^1H$ (CD$_3$COCD$_3$): 1.24 (t, 3H, CH$_3$ ethyl), 1.89 (s, 3H, CH$_3$ amide), 2.61 (q, 2H, CH$_2$ ethyl), 2.86 (t, 2H), 3.45 (q, 2H, CH$_2$—N), 3.78 (5, 3H, OC$\underline{H}_3$), 5.8 (broad s, 1H, H—N amide), 6.76 (dd, 1H, H-6), 6.96 (d, 1H, H-4), 7.14 (d, 1H, H-7), 8.4 (s, 1H1, H—N$^-$indole)

COMPOUNDS ACCORDING TO THE INVENTION

EXAMPLE 1

Procedure: Ref. J. Chem. Soc. Perkin Trans. 1 1992, p461

To a solution of melatonin (1 g) in benzene (150 ml) at 0° C. is added pentafluoropropionic anhydride (8 ml). After reacting for 15 minutes at 0° C., the solvent is evaporated off and compound 1 is recrystallized from petroleum ether (2.23 g, 77%).

Formula: $C_{22}H_{13}N_2O_5F_{15}$ M=670.30 g·mol$^{-1}$ NMR: $^1H$ (CDCl$_3$): 2.41 (1H, m, H-4' α or β), 2.86 (1H, m, H-4' α or β), 3.85 (3H, s, OCH$_3$), 3.98 and 4.20 (2H, m, H-5' α and β), 4.19 (1H, s, Hvin.), 6.11 (1H, s, Hvin.), 6.76 (1H, d, H-4), 6.97 (1H, s, H-2), 6.99 (1H, dd, H-6), 8.07 (1H, d, H-7)

EXAMPLE 2

Procedure: Ref. J. Chem. Soc. Perkin Trans. 1 1992, p461

To a solution of melatonin (750 g) in benzene (120 ml) at 0° C. is added trifluoroacetic anhydride (8 ml). After reacting for 15 minutes at 0° C., the solvent is evaporated off and compound 2 is recrystallized from petroleum ether.

Formula: $C_{15}H_{13}N_2O_5F_9$ M=520.30 g·mol$^{-1}$ NMR: $^1H$ (CDCl$_3$): 2.28 (1H, m, H-4' α or β), 2.60 (1H, m, H-4' α or β), 3.85 (3H, s, OCH$_3$), 3.98 and 4.20 (2H, m, H-5' α and β), 4.19 (1H, s, Hvin.), 6.13 (1H, broad s, Hvin.), 6.78 (1H, d, H-4), 6.98 (1H, s, H-2), 7.00 (1H, dd, H-6), 8.13 (1H, d, H-7)

EXAMPLE 3

To a cooled (0°–5° C.) solution of 2-bromomelatonin (100 mg) in benzene (10 ml) is added pentafluoropropionic anhydride (PFPA, 0.5 ml). After reacting for 15 minutes, the reaction medium is evaporated under reduced pressure. The crude product is then flash-chromatographed (eluent: 30/70 EtOAc/petroleum ether). Compound 3 elutes first.

Yield=65%. Formula: $C_{16}H_{13}N_2O_3F_5$ M=376.28 g·mol$^{-1}$ Melting point : 178°–80° C. NMR: $^1H$ (CDCl$_3$): 2.43 (m, 2H, H-4'), 3.79 (s, 3H, OC$\underline{H}_3$), 4.3–4.4 (m, 2H, H-5'), 4.45 (s, 1H, H-vin), 6.11 (s, 1H, H-vin), 6.8–6.9 (m, 3H, H-4,6,7), 9.1 (broad s, 1H, H-1)

$^{13}C$ (CDCl$_3$): 179.9 (C-2), 156.7 (C-5), 156.4 (CORI), 145.6 (C-2'), 134.7 (C-7a), 131.6 (C-3a), 114.3 (C-7), 110.9 and 111 (C-4,6), 101.3 (C vin), 57.5 (C-3), 55.9 (OCH$_3$), 46.6 (C-5'), 33.7 (C-4')

Mass spectrum: Exact mass: m/z:376(M$^+$·), 229 (M—COC$_2$CF$_5$), calculated: 376.0846 187.147 (COC$_2$CF$_5$$^+$), 119 (C$_2$CF$_5$$^+$) found: 376.0847

Infra-red: (cm$^{-1}$)

3197 (m), 1703(s), 1630 (m), 1499(m)

EXAMPLE 4

To a cooled (0°–5° C.) solution of 2-bromomelatonin (100 mg) in benzene (10 ml) is added trifluoroacetic anhydride (TFAA, 0.5 ml). After reacting for 15 min, the reaction medium is evaporated under reduced pressure. The crude product is then flash-chromatographed (eluent: 30/70 EtOAc/petroleum ether). Compound 4 elutes first.

Yield=70%. Formula: $C_{15}H_{13}N_2O_3F_3$ M=326.28 g·mol$^{-1}$ Melting point: 168°–70° C. NMR: $^1H$ (CDCl$_3$): 2.40 (m, 2H, H-4'), 3.79 (s, 3H, OC$\underline{H}_3$), 4.19 (t, 8.6 Hz, 1H, H-5' α or β), 4.44 (m, 1H, H-5' α or β), 4.45 (s, 1H, H-vin), 6.10 (s, 1H, H-vin), 6.8–6.9 (m, 3H, H-4,6,7), 8.91 (broad s, 1H, H-1)

$^{13}C$ (CDCl$_3$): 179.2 (C-2), 156.7 (C-5), 145.5 (C-2'), 134.7 (C-7a), 131.6 (C-4a), 114.3 (C-7), 111.1 and 110.7 (C-4,6), 100.8 (C vin), 57.6 (C-3), 55.9 (OCH$_3$), 46.9 (C-5'), 33.7 (C-4')

Mass spectrum: Exact mass: m/z:326(M$^+$·), 229 (M—COCF3) calculated: 326.0878 187.69. (CF$_3$$^+$) found: 326.0877

Infra-red: (cm$^{-1}$)

3181 (m), 1717(b),
1633, 1607, 1498

EXAMPLE 5

1st method

Compound 4 (220 mg) is added to a saturated solution of $K_2CO_3$ in aqueous methanol (40%, 10 ml). The medium is left stirring for 2 hours at room temperature. The methanol is then evaporated off. The crude product is extracted with dichloromethane and then washed with water and dried over sodium sulphate. Compound 5 is recovered after evaporation of the solvent. Yield=90%.

2nd method

A solution of 2-oxomelatonin (2 mmol) in toluene (25 ml) is brought to reflux. Dimethyl sulphate (2 eq) is then added while hot, and the stirring and temperature are maintained for two hours. The medium is then heated overnight without stirring. After removal of the toluene, the crude product is taken up in water and then extracted with ethyl acetate. Compound 5 is recovered after evaporation of the solvent (yield 40%).

Formula: $C_{13}H_{14}N_2O_2$ M=230.27 g·mol$^{-1}$ NMR: $^1$H (CDCl$_3$): 1.76 (s, 3H, CH$_3$), 2.29 (m, H, H-4' $\alpha$ or $\beta$), 2.66 (m, H, H-4' $\alpha$ or $\beta$), 3.77 (s, 3H, OCH$_3$), 4.15 (m, 2H, H-5'), 6.64 (d, 1.3 Hz, 1H, H-4), 6.77 (dd, 8.6 and 1.3 Hz, 1H, H-6), 6.87 (d, 8.6 Hz, 1H, H-7), 8.87 (broad s, 1H, H-1)

$^{13}$C (CDCl$_3$): 178.5 (N-C=O), 170.7 (C=N), 156.5 (C-5), 134.3 and 132.4 (C-3a and C-7a), 113.6, 110.4 and 110.4 (C-4,6,7), 67.7 (C-3), 60.5 (C-5'), 55.9 (OCH$_3$), 36.1 (C-4'), 15.7 (CH$_3$)

Mass spectrum: m/z: 230 (M$^+$·), 189.174

EXAMPLE 6

To a solution of compound 5 (170 mg, 0.74 mmol) in pyridine (1 ml) is added acetic anhydride (1.1 eq, 0.12 ml). Part of the pyridine is removed under vacuum. The crude product is then taken up in water and extracted with dichloromethane. After flash chromatography on silica (50/50 EtOAc/pet. ether), compound 6 is obtained (70%).

Formula: $C_{15}H_{16}N_2O_3$ M=272.30 g·mol$^{-1}$ NMR: $^1$H (CDCl$_3$): 2.20 (s, 3H, CH$_3$ amide), 2.31 (t, 2H, H-4'), 3.75 (s, 3H, OCH$_3$), 3.96 (s, 1H, H-vin), 4.0 (m, 1H, H-5' $\alpha$ or $\beta$), 4.14 (m, 1H, H-5' $\alpha$ or $\beta$), 5.81 (broad s, 1H, H-vin), 6.8–6.9 (m, 3H, H-4,6,7), 9.36 (broad s, 1H, H-1)

$^{13}$C (CDCl$_3$): 179.4 (C-2), 170 (N—CO—Me), 156.9 (C-5), 148 (C-2'), 136.5 (C-7a), 133.7 (C-3a), 114.3 (C-7), 111.8 and 110.9 (C-4,6), 94.7 (C vin), 59.3 (C-3), 56.1 (OCH$_3$), 48.5 (C-5'), 33.4 (C-4'), 24.8 (CH$_3$ amide).

Mass spectrum: Exact mass: m/z:272(M$^+$·), 203.168 calculated: 272.1160 found: 272.1158

EXAMPLE 7

To a solution of compound 5 (1 nmol) in pyridine (1 ml) is added propionic anhydride (1.1 eq). Part of the pyridine is removed under vacuum. The crude product is then taken up in water and extracted with dichloromethane. After flash chromatography on silica (50/50 EtOAc/pet. ether), compound 7 is obtained.

Formula: $C_{16}H_{18}N_2O_3$ M=300.30 g·mol$^{-1}$ NMR: $^1$H (CDCl$_3$): 1.21 (t, 3H, CH$_3$ ethyl), 2.31 (t, 2H, H-4'), 2.5 (q, 2H, OCH$_2$), 3.76 (8, 3H, OCH$_3$), 3.93 (m, 1H, H-5' $\alpha$ or $\beta$), 4.14 (s, 1H, H-vin), 4.3 (m, 1H, H-5' $\alpha$ or $\beta$), 5.91 (broad s, 1H, H-vin), 6.94–7.0 (m, 3H, H-4,6,7), 8.82 (broad s, 1H, H-1)

$^{13}$C (CDCl$_3$): 179 (C-2), 173 (N—CO—Me), 156.4 (C-5), 145.8 (C-2'), 134.6 (C-7a), 132.4 (C-3a), 113.7 (C-7), 111.0 and 110.0 (C-4,6), 96 (C vin), 58.5 (C-3), 56.0 (OCH$_3$), 47.0 (C-5'), 33 (C-4'), 29.7 (CH$_2$ amide), 8.75 (CH$_3$ amide).

Mass spectrum: Exact mass: m/z:286(M$^+$·), 230.189 calculated: 286.1317 found: 286.1317

EXAMPLE 8

To a solution of compound 5 (1 mmol) in pyridine (1 ml) is added butyric anhydride (1.1 eq). Part of the pyridine is removed under vacuum. The crude product is then taken up in water and extracted with dichloromethane. After flash chromatography on silica (50/50 EtOAc/pet. ether), compound 8 is obtained.

Formula: $C_{17}H_{20}N_2O_3$ M=300.30g·mol$^{-1}$ NMR: $^1$H (CDCl$_3$): 1.03 (t, 3H, CH$_3$ amide), 1.77 (m, 2H, C$_2$Me), 2.22 (t, 2H, H-4'), 2.47 (t, 2H, CH$_2$N amide), 3.77 (B, 3H, OCH$_3$), 3.9 (m, 1H, H-5' $\alpha$ or $\beta$), 4.15 (s, 1H, H-vin), 4.3 (m, 1H, H-5' $\alpha$ or $\beta$), 5.95 (broad s, 1H, H-vin), 6.7–7 (m, 3H, H-4,6,7), 8.4 (broad s, 1H, H-1)

Mass spectrum: Exact mass: m/z:300(M$^+$·), 230.189 calculated: 300.1474 found: 300.1470

EXAMPLES 9 AND 10

To a cooled (0°–5° C.) solution of 2,6- and 2,4-dibromomelatonin (100 mg) in benzene (10 ml) is added pentafluoropropionic anhydride (PFPA, 0.5 ml). After reacting for 15 min, the reaction medium is evaporated under reduced pressure. Flash chromatography allows compound 10 to be recovered (35%) (eluent: 20/80 EtOAc/petroleum ether) followed by compound 9 (48%) (eluent: 40/60 EtOAc/petroleum ether).

Compound 9

Formula: $C_{16}H_{12}N_2O_3F_5Br$ M=455.18 g·mol$^{-1}$ NMR: $^1$H (CDCl$_3$): 2.27 (m, 1H, H-4' $\alpha$ or $\beta$), 3.01 (m, 1H, H-4' $\alpha$ or $\beta$), 3.88 (s, 3H, OCH$_3$), 4.43 (m, 2H, H-5'), 4.47 (8, 1H, H-vin), 6.11 (s, 1H, H-vin), 6.8–6.9 (m, 2H, H-6,7), 9.35 (broad s, 1H, H-1)

$^{13}$C (CDCl$_3$): 179.4 (C-2), 153 (C-5), 142 (C-2'), 136.2 (C-7a), 124.9 (C-3a), 112.7, 109.5 and 110 (C-4,6,7), 100.8 (C vin), 59.1 (C-3), 56.9 (OCH$_3$), 46.9 (C-5'), 28.9 (C4')

Mass spectrum: Exact mass: m/z:456, 454, 267, 265 calculated: 453.9951 found: 453.9940

Compound 10

Formula: $C_{16}H_{12}N_2O_3F_5Br$ M=455.18 g·mol$^{-1}$ NMR: $^1$H (CDCl$_3$): 2.40 (m, 2H, H-4'), 3.86 (s, 3H, OCH$_3$), 4.28 and 4.5 (m, 2H, H-5'), 4.43 (s, 1H, H-vin), 6.13 (s, 1H, H-vin), 6.77 (s, 1H, H-4), 7.19 (s, 1H, H-7), 8.6 (broad s, 1H, H-1)

$^{13}$C (CDCl$_3$): 179 (C-2), 153 (C-5), 145 (C-2'), 135.4 (C-7a), 130.2 (C-3a), 115.5, 112.7 and 109.2 (C-4,6,7), 101.6 (C vin), 57.4 (C-3), 57.1 (OCH$_3$), 46.5 (C-5'), 33.7 (C-4')

Mass spectrum: Exact mass: m/z:456, 454, 267, 265 calculated: 453.9951 found: 453.9948

EXAMPLE 11

The procedures of Examples 5 and then 6 are repeated, with compound 9 as the starting material, and compound 11 is obtained in similar yields.

Formula: $C_{15}H_{15}N_2O_3Br$ M=351.20 g·mol$^{-1}$ NMR: $^1$H (CDCl$_3$): 2.29 (m, 2H, H-4'), 2.30 (s, 3H, CH$_3$CO) 3.86 (s, 3H, OCH$_3$), 4.10 (m, 2H, H-5'), 4.16 (s, 1H, H-vin), 5.94 (s, 1H, H-vin), 6.84 (m, 2H, H-6,7), 9.47 (broad s, 1H, H-1)

Mass spectrum: Exact mass: m/z: 352, 350, 310 calculated: 350.0266 308, 267, 189 found: 350.0264

EXAMPLE 12

The procedures of Examples 5 (1st method) and then 6 are repeated, with compound 10 as the starting material, and compound 12 is obtained in similar yields.

Formula: $C_{15}H_{15}N_2O_3Br$ M=351.20 g·mol$^{-1}$ NMR: $^1$H (CDCl$_3$) : 2.23 (m, 2H, H-4'), 2.30 (s, 3H, CH$_3$CO) 3.82 (s, 3H, OCH$_3$), 3.94 (m, 2H, H-5'), 4.09 (s, 1H, H-vin), 5.75 (s, 1H, H-vin), 6.93 (m, 1H, H-4), 7.06 (m, 1H, H-7), 10.31 (broad s, 1H, H-1)

EXAMPLE 13

The procedure of Example 3 is repeated, with 1-methyl-2-bromomelatonin as the starting material, and compound 13 is obtained in similar yields:

Formula: $C_{17}H_{15}N_3O_3F_5$ M=390.30 g·mol$^{-1}$ NMR: $^1$H (CDCl$_3$): 2.36 (m, 2H, H-4'), 3.21 (s, 3H, N—CH$_3$), 3.80 (s, 3H, OCH$_3$), 4.36 (5, 1H, H-vin), 4.3–4.5 (m, 2H, H-5'), 6.01 (s, 1H, H-vin), 6.80–6.90 (m, 3H, H-4,6,7)

Mass spectrum: m/z:390(M$^+$·), 243 (M—COC$_2$CF$_5$)

EXAMPLE 14

The procedure of Example 5 (first method) is repeated, with compound 13 as the starting material, and compound 14 is obtained in similar yields.

Formula: $C_{14}H_{16}N_2O_2$ M=244.29 g·mol$^{-1}$ NMR: $^1$H (CDCl$_3$): 1.67 (s,-3H, CH$_3$), 2.26 (m, H, H-4' α or β), 2.60 (m, H, H-4' α or β), 3.25 (s, 3H, NCH$_3$), 3.78 (s, 3H, OCH$_3$), 4.13 (m, 2H, H-5'), 6.69 (m, 1H, H-4), 6.83 (m, 2H, H-6,7), 10.31 (broad s, 1H, H-1)

EXAMPLE 15

The procedure of Example 6 is repeated, with compound 14 as the starting material, and compound 15 is obtained in similar yields.

Formula: $C_{16}H_{18}N_2O_3$ M=286.33 g·mol$^{-1}$ NMR: $^1$H (CDCl$_3$): 2.27 (s,3H, CH$_3$CO), 2.3 (m, 2H, H-4$^1$), 3.17 (s, 3H, NCH$_3$), 3.78 (s, 3H, OCH$_3$), 4 and 4.14 (m, 2H, H-5'), 4.07 (s, 1H, H-vin), 5.86 (s, 1H, H-vin), 6.6–6.9 (m, 3H, H-4,6,7).

$^{13}$C (CDCl$_3$): 176 (C-2), 170 N—CO—Me), 156 (C-5), 145 (C-2'), 140 (C-7a), 137 (C-3a), 113 (C-7), 111 and 109 (C-4,6), 96 (C vin), 58 (C-3), 55 (OCH$_3$), 47 (C-5'), 32 (C-4'), 26 (N—CH$_3$), 24.8 (CH$_3$ amide).

Mass spectrum : m/z:286(M$^+$·), 244, 203, 188

EXAMPLE 16

To compound 4 (342 mg, 1.05 mol) dissolved in dichloromethane (20 ml) is added, at 0° C., Meerwein's reagent (1.2 eq, 1.2 ml of 1M solution of BF$_4$Et$_3$O in CH$_2$Cl$_2$). The reaction mixture is stirred for 48 h under a nitrogen atmosphere. After hydrolysis, the crude product is extracted with dichloromethane. The crude product is then flash-chromatographed (20/80 EtOAc/pet. ether). Compound 16 is eluted first. Yield=40%. 35% of the starting material are then recovered.

Formula: $C_{17}H_{17}N_2O_3F_3$ M=354.32 g·mol$^{-1}$ NMR: $^1$H (CDCl$_3$): 1.38 (t, 3H, CH$_3$ ethyl), 2.35 (t, 2H, H-4'), 3.80 (s, 3H, OCH$_3$), 4.22 (q, 2H, OCH$_2$), 4.40 (s, 1H, H-vin), 4.40 (t, 2H, H-5'), 5.97 (s, 1H, H-vin), 6.74 (d, 1H, H-4), 6.84 (dd, 1H, H-6), 7.26 (m, 1H, H-7), $^{13}$C (CDCl$_3$): 179.5 (C-2), 157.3 (C-5), 146.7 (C-2'), 144.4 (C-7a), 138.8 (C-3a), 118.9 (C-7), 113.6 and 109.4 (C-4,6), 99.9 (C-vin), 65.6 (OCH$_2$), 60.5 (C-3), 55.7 (OCH$_3$), 46.8 (C-5'), 32.3 (C-4'), 14.1 (CH$_3$ ethyl).

Mass spectrum : m/z: 354, 326, 283, 187

EXAMPLE 17

The procedure of Example 5 (first method) is repeated, with compound 16 as the starting material, and compound 17 is obtained in similar yields.

Formula: $C_{15}H_{18}N_2O_2$ M=258.32 g·mol$^{-1}$ NMR: $^1$H (CDCl$_3$): 1.39 (t, 3H, CH$_3$ ethyl), 1.62 (s, 3H, CH$_3$), 2.27 (m, H, H-4' α or β), 2.55 (m, H, H-4' α or β), 3.77 (s, 3H, OCH$_3$), 4.13 (t, 2H, H-5'), 4.44 (q, 2H, OCH$_2$), 6.66 (d, 1H, H-4), 6.81 (dd, 1H, H-6), 7.26 (d 8.6 Hz, 11, H-7)

Mass spectrum m/z: 258, 217, 189, 174

EXAMPLE 18

The procedure of Example 6 is repeated, with compound 17 as the starting material, and compound 18 is obtained in similar yields.

Formula: $C_{17}H_{20}N_2O_3$ M=300.35 g·mol$^{-1}$ NMR: $^1$H (CDCl$_3$): 1.38 (t, 31, CH$_3$ ethyl), 2.27 (s, 3H, CH$_3$CO), 2.3 and 2.5 (m, 2H, H-4'), 3.78 (s, 3H, OCH$_3$),4-4, 14 (m, 2H, H-5'), 4.13 (s, 1H, H-vin), 4.44 (q, 2H, OCH$_2$), 5.8 (s, 1H, H-vin), 6.74 (d, 1H, H4), 6.81 (dd, 1H, H-6), 7.24 (d, 1H, H-7).

Mass spectrum: m/z: 300, 258, 243, 230

EXAMPLE 19

The procedure of Example 3 is repeated, with 2-ethylmelatonin as the starting material, and compound 19 is obtained in similar yields.

Formula: $C_{18}H_{17}N_2O_2F_5$ M=388.33 g·mol$^{-1}$ NMR: $^1$H(CDCl$_3$): 1.37 (t, 3H, CH$_3$ ethyl), 2.6 (q, 2H, CH$_2$ ethyl), 2.87 (m, 2H, H-4'), 3.82 (s, 3H, OCH$_3$), 4.29 (s, 1H, H-vin), 4.51 (m, 2H, H-5'), 5.93 (s, 1H, H-vin), 6.98 (dd, 1H, H-6), 7.15 (d, 1H, H-4), 7.59 (d, 1H, X-7).

Mass spectrum : m/z: 388, 212

EXAMPLE 20

The procedure of Example 5 (first method) is repeated, with compound 19 as the starting material, and compound 20 is obtained in similar yields.

Formula: $C_{15}H_{18}N_2O$ M=242.32 g·mol$^{-1}$ NMR: $^1$H (CDCl$_3$): 1.34 (t, 3H, CH$_3$ ethyl), 1.49 (s, 3H, CH$_3$), 2.37 (m, 2H, CH$_2$ ethyl), 2.5–2.6 (m, 2H, H-4'), 3.80 (s, 3H, OCH$_3$), 4.21 (m, 2H, H-5'), 6.75 (d, 1X, H-4), 6.87 (dd, 1H, H-6), 7.50 (d, 1H, H-7).

EXAMPLE 21

The procedure of Example 6 is repeated, with compound 20 as the starting material, and compound 21 is obtained in similar yields.

Formula: $C_{17}H_{20}N_2O_2$ M=284.35 g·mol$^{-1}$ NMR: $^1$H (CDCl$_3$): 1.34 (t, 3H, CH$_3$ ethyl), 2.30 (s, 3H, CH$_3$CO), 2.2–2.3 (m, 2H, H-4'), 2.53 (m, 2H, CH$_2$ ethyl), 3.79 (s, 3H, OCH$_3$), 4.05 (m, 2H, H-5'), 4.07 (s, 1H, H-vin), 5.75 (8, 1H, H-vin), 6.79 (d, 1H, H-4), 6.84 (dd, 1H, H-6), 7.48 (d, 1H, H-7).

$^{13}$C(CDCl$_3$): 184 (C-2), 170 (CO), 159 (C-5), 154.8 (C-2'), 148 and 144.7 (C-3a and C-7a), 120.5, 112.8 and 108.9 (C4,6,7), 95.1 (Cvin), 67.5 (C-3), 55.8 (CH$_3$O), 47.8 (C-5'), 30.5 (C-4'), 24.7 (CH$_3$ amide), 22.8 (CH$_2$ ethyl), 10.6 (CH$_3$ ethyl).

Mass spectrum: m/z: 284, 242, 227, 213

EXAMPLE 22

To a cooled (0-5° C.) solution of 2-bromo-Nβ-acetyltryptamine in benzene is added pentafluoropropionic anhydride (PFPA). After reacting for 15 min, the reaction medium is evaporated under reduced pressure. The crude product is then flash-chromatographed (eluent: 20/80 EtOAc/petroleum ether). Compound 22 elutes first.

Formula: $C_{15}H_{11}N_2O_2F_5$ M=346.26 g·mol$^{-1}$ Fusion point: 178°–80° C. NMR: $^1$H(CDCl$_3$): 2.43 (m, 2H, H-4'), 4.27 and 4.51 (m, 2H, H-5'), 4.43 (s, 1H, H-vin), 6.10 (s, 1H, H-vin), 6.99–7.31 (m, 4H, H-4,5,6,7), 8.89 (broad s, 1H, H-1)

$^{13}$C(CDCl$_3$): 179 (C-2), 156 (CORf), 145 (C-2'), 141.5 (C-5), 130 and 129.5 (C-7a and C-3a), 124.5, 123.6 and 110.6 (C-4,6,7), 101.4 (C vin), 57.5 (C-3), 46.5 (C-5'), 33.6 (C-4')

Mass spectrum: Exact mass: m/z: 346(M$^+$·), 227 calculated: 346.0740 199, 157 found: 346.0736

EXAMPLE 23

The procedures of Example 5 (first or second method) are repeated, with compound 22 as the starting material, and compound 23 is obtained in similar yields.

Formula: $C_{12}H_{12}N_2$ O M=200.24 g·mol$^{-1}$ NMR: $^1$H (CDCl$_3$): 1.78 (s, 3H, CH$_3$), 2.33 (m, H, H-4' a or b), 2.66 (m, H, H-4' a or b), 4.19 (m, 2H, H-5'), 7.02–7.28 (m, 4H, H4,5,6,7), 9.81 (broad s, 1H, H-1)

$^{13}$C (CDCl$_3$) : 179 (N—C=O), 171 (C=N), 141, 131, 128, 123, 110, 85.5, 67.7 (C-3), 60.5 (C-5'), 36.1 (C-4'), 15.7 (CH$_3$)

EXAMPLE 24

To a solution of compound 23 in pyridine is added acetic anhydride (1.1 eq). Part of the pyridine is removed under vacuum. The crude product is then taken up in water and extracted with dichloromethane. After flash chromatography on silica (40/60 EtOAc/pet. ether), compound 24 is obtained.

Formula: $C_{14}H_{14}N_2O_2$ M=242.28 g·mol$^{-1}$ NMR: $^1$H (CDCl$_3$): 2.30 (s, 3H, CH$_3$CO), 2.31 (m, 2H, H-4'), 3.92 and 4.20 (m, 2H, H-5α and β), 4.14 (s, 1H, H vin.), 5.92 (broad s, 1H, H vin.), 6.98–7.26 (m, 4H, H-4,5,6,7), 9.24 (broad s, 1H, NH).

Mass spectrum: Exact mass: m/z: 272(M$^+$·), 203, 168 calculated: 242.1055 199, 157 found: 242.1057

EXAMPLE 25

The procedures of Example 3 are repeated, with 2-ethyl-Nβ-acetyltryptamine as the starting material, and compound 25 is obtained in similar yields.

Formula: $C_{17}H_{15}N_2OF_5$ M=358.31 g·mol$^{-1}$ NNR: $^1$H (CDCl$_3$): 1.41 (t, 3H, CH$_3$ ethyl), 2.59 (q, 2H, CH$_2$ ethyl), 2.94 (m, 2X, X-4'), 4.28 (s, 1H, H-vin), 4.55 (t, 2H, H-5'), 5.93 (s, 1H, H-vin), 7.5–7.7 (m, 4H, H-4,5,6,7).

Mass spectrum: m/z: 358(M$^+$·), 329, 211, 182

EXAMPLE 26

The procedure of Example 5 (first method) is repeated, with compound 25 as the starting material, and compound 26 is obtained in similar yields.

Formula: $C_{14}H_{16}N_2$ M=212.29 g·mol$^{-1}$ NMR: (CDCl$_3$): 1.36 (t, 3H, CH$_3$ ethyl), 1.46 (s, 3H, CH$_3$), 2.41 (q, 2H, CH$_2$ ethyl), 2.63 (m, 2H, H-4'), 4.19 (m, 2X, H-5'), 7.2–7.5 (m, 4H, H4,5,6,7).

EXAMPLE 27

The procedure of Example 24 is repeated, with compound 26 as the starting material, and compound 27 is obtained in similar yields.

Formula : $C_{16}H_{18}N_2O$ M=254.33 g·mol$^{-1}$ NMR: $^1$H (CDCl$_3$): 1.37 (t, 3H, C$_3$ ethyl), 2.25 (q, 2H, CH$_2$ ethyl), 2.30 (s, 3H, CH$_3$CO), 2.5 (m, 2X, H-4'), 3.97 (s, 1H, H vin.), 4.05 (t, 2H, H-5'), 5.75 (broad s, 1H, H vin.), 7.21–7.57 (m, 4H, H-4,5,6,7).

$^{13}$C (CDCl$_3$): 186.7 (C-2), 169.7 (C=O), 154 (C-7a), 144 (C-2'), 143 (C-3a), 128.9, 126, 121.7 and 120.3 (C-4,5,6,7), 95 (C vin.), 67.4 (C-3), 47.8 (C-5'), 30.4 (C-4'), 24.7 (CH$_3$ amide), 22.7 (CH$_2$ ethyl), 10.6 (CH$_3$ ethyl)

Mass spectrum: m/z: 254(M$^+$·), 212, 183

EXAMPLE 28

Compound 27 (30 mg) is dissolved in methanol (5 ml), followed by addition of sodium borohydride (35 mg); the medium is stirred for one hour. After evaporation of the methanol, the mixture is taken up in dichloromethane and washed with water. The crude product is then separated on a silica plate (eluent: 50/50 ethyl acetate/petroleum ether).

Formula: $C_{16}H_{20}N_2O$ M=256.33 g·mol$^{-1}$ NMR: $^1$H (CDCl$_3$): 0.96 (t, 3H, CH$_3$ ethyl), 1.39 (m, 2H, CH$_2$ ethyl), 2.20 (s, 3H, CH$_3$CO), 2.32 (m, 2H, H-4'), 3.42 (m, 1H, H-2), 3.72 (t, 2H, H-5'), 4.29 (s, 1H, H vin.), 4.72 (broad s, 1H, NH), 6.06 (broad s, 1H, H vin.), 6.78–7.02 (m, 4H, H-4,5, 6,7). Mass spectrum: m/z: 256(M$^+$·), 185, 130

BIOLOGICAL ACTIVITY

The hypnotic and sedative effects of the derivatives, according to the invention, prepared above (whose test results are shown in Table IV below) were compared with those of three reference products, diazepam, pentobarbital sodium and melatonin, in 10- to 18-day-old chicks of the strain chair label JA657. The animals are subjected to programmes of alternate lighting consisting of 12 h of darkness (20.00 h to 8.00 h) and 12 h of light (8.00 h to 20.00 h). The room temperature is 25° C. during the first week of rearing the chicks and 22° C. from the second week. During the day, the lighting is provided by a 20W×60 cm neon lamp placed 30 cm above the floor of the vivarium. During the tests, the live weight of the chicks ranged between 85 and 120 g. The tests are performed between 10.00 h and 14.00 h. The chicks are allotted in groups of 3 into identical 30 cm×50 cm×30 cm vivaria. The test products are administered intramuscularly (IM) into the pectoralis major muscle as an aqueous-ethanolic solution (50/50 V/V ethanol/ distilled water mixture), in a proportion of 0.2 ml of ethanolic solution per 100 g of live weight. The doses administered for the test products (novel compounds of the invention and reference substances) are equimolar (1 μmol/ 100 g of live weight, or 2 μg/100 g for a few compounds). The placebo corresponds to 0.2 ml of the ethanol/distilled water mixture (aa) . Since ethanol is used as solvent, its effect was compared beforehand with that of physiological saline (NaCl solution at a concentration of 0.9 p. 100) or distilled water.

The aqueous-ethanolic solutions of the test products were prepared at the time of use by successive dilution of a stock solution, obtained from 10 μmol of accurately weighed product, to which is added 1 ml of pure ethanol and which is agitated by ultrasound and then made up to 2 ml with 1 ml of distilled water for an injectable preparation. Table I shows the results obtained after IM administrations of 1 μmol of the test products, dissolved in 0.2 ml of the ethanol/distilled water mixture, per 100 g of live weight. For each chick, the volume injected is adjusted, according to the actual live weight, to 0.2 ml per 100 g of live weight. For a few compounds, the doses administered were 2 μmol/100 g of live weight.

The parameters observed are the locomotor activity and the state of consciousness of the chicks over 2 h, which is equivalent to 6 theoretical wake-sleep cycles for a chick of this age. They are recorded by video camera for 90 minutes, the first 30 minutes being the time for adaptation to the device.

Five stages of alertness were defined:

stage 1: active wakefulness;

stage 2: animal lying down, head maintained with tonicity, eyes open;

stage 3: light sleep, animal drowsy: eyes closed with intermittent opening, immobile posture not modified by stimulation;

stage 4: deep sleep lying down: relaxation of the neck, characteristic posture of the head under the wing or thrown backwards;

stage 5: sleeping standing up: eyes closed, immobile, head dropped (catatonic).

These five stages correspond approximately to the stages of alertness and sleep defined in the examination of the electroencephalographic traces in this species. The correspondence is as follows:

deep sleep lying down: stage 4 ="slow wave sleep"0 (SWS)

sleeping standing up="sleep-like state I" (SLSI) The drowsy stage 3 could correspond to paradoxical phases of sleep, with movement of the head, for example.

The chicks are observed by a trained observer with continuous video monitoring for at least 1 hour after the animals wake up.

Two stimuli were used to confirm the observations of the behaviour of the chicks at regular intervals:

the noise caused by tapping a plastic object on the glass of the vivarium, comparable to that of the beak of a chick on the glass, corresponds to a moderate stimulus. It is performed at each period of observation (i.e. every 5 minutes);

and the presentation of a metal feeder filled with the usual feed, left in the vivarium for 2 minutes. This is a powerful stimulus which calls upon sight, hearing and smell. It is performed every 15 minutes, that is to say at least 6 times in each test.

The wakeful state is defined by the appearance of the conscious elaborate behaviour of searching for and consumption of food and drink.

The sleep time (ST) is defined by the sum of the durations of the phases of light sleep (stage 3), deep sleep (stage 4) and sleep standing up (stage 5). The sedation time, following waking up, corresponds to stage 2.

The falling-asleep time (FAT) is equal (to the nearest minute) to the time required to pass from the state of active wakefulness (stage 1) to a non-alert state (stages 3, 4 and 5).

The hypnotic and sedative effects of the test products on the diurnal activity of 10- to 18-day-old chicks subjected to a programme of permanent lighting from birth to the 6th day, and then to a programme of alternate lighting of 12 h of day (8.00 h–20.00 h) and 12 h of darkness (20.00 h–8.00 h) are given in Table IV below.

The tests are performed during the day between 10.00 h and 14.00 h. For each test product, several series of measurements were made on batches of 3 animals, each value indicated being the average of 1 or more batches of 3 animals.

The following values were measured:

FAT: falling-asleep time equal to the time required to pass from the state of active wakefulness to a non-alert state;

ST: sleep time, equal to the duration of the period of sleep ranging from the point of having fallen asleep to the point of waking up;

Sedation time: following waking up, period of inactivity corresponding to stage 2 defined above.

TABLE IV

| COMPOUND | DOSE μM/100 g | FAT (minutes) | ST (minutes) | Sedation time (minutes) |
| --- | --- | --- | --- | --- |
| 1 | 1 | 1–6 | 48.3 to 100* | |
| 2 | 1 | 2–8 | 50 to 100* | |
| 3 | 1 | 8 | 7 | 38 |
| A | 1 | 3 | 20 | 7 |
| 6 | 1 | 2–5 | 10–35 | 3–25 |
| 6 | 2 | 5–9 | 55–62 | 2–5 |
| 7 | 2 | 4 | 55–85 | NA |
| 8 | 2 | 10 | 50–65 | NA |
| 9 and 10 | 2 | 5–10 | 10–20 | 15–30 |
| 11 and 12 | 2 | 8–10 | 20–30 | 5–10 |
| 13 | 2 | 5–10 | 15–30 | 15–30 |
| 15 | 2 | 3–6 | 60–65 | NA |
| 16 | 2 | 4 | 30 | 35 |
| 18 | 2 | 3–8 | 55–75 | NA |
| 19 | 2 | 5 | 25 | 30 |
| 21 | 2 | 2–5 | 45–70 | 2–8 |
| Placebo | 1 | NA | NA | NA |
| Melatonin | 1 | NA–17 | NA to 25 | |
| Pentobarbital | 1 | 13 | 36.3 | NA |
| Diazepam | 1 | 2–7 | 30–57 | 2–65 |

NA = not applicable, animals alert or absence of sedation
*durations of inactivity corresponding to the sum of the sleep time and of the sedation time.

A marked sedation, following waking up, was for compounds 1, 2, 3, 4, 9, 10, 13, 16 and 19, fluoro derivatives.

Under the conditions in which the test is perschedule of administration during the phase in which the animals are in light), the hypnosedative activity of melatonin is low (administration at 10.00 h) or even zero (administration at 14.00 h); the results observed depend on the time of administration of the melatonin. On the other hand, for all the other products tested, the results are independent of the time of administration during the lighting phase (between 10.00 h and 14.00 h).

By successively subjecting chicks to programmes of alternate and permanent lighting, we have demonstrated experimentally that melatonin has no direct hypnotic activity intrinsic to its structure. Its hypnotic activity depends on the activity of the enzyme N-acetyltransferase (NAT) in the pineal gland of the chick at the moment of administration of the melatonin. The enzyme NAT is an acetylation enzyme. In the presence of the enzyme NAT in the pineal gland of the chick, the IM administration of melatonin induces a hypnotic effect of high intensity (sleep time of between 250 and 300 minutes for a dose equal to 1 μmol of melatonin/100 g of live weight). Melatonin is thus the precursor of acetylated metabolites having direct hypnotic activity, among which the compound 6 features.

Thus, the derivatives of the invention, described above, appear to be acylation derivatives of melatonin or of derivatives of similar chemical structure. In contrast with melatonin, all of the derivatives of the invention, described above, have direct hypnotic or sedative activities, which are independent of the time of administration, via the IM route in chicks.

The results obtained show, for the derivatives according to the invention, a hypnotic effect which is superior to that of the reference products (pento-barbital, melatonin) and equivalent to that of diazepam.

The derivatives according to the invention are thus particularly advantageous for the treatment of diseases associated with disorders of melatonin activity.

The present invention thus relates to the derivatives of general formula I, as defined above, for their use in therapy, especially for the treatment of depression and psychiatric disorders, in particular stress, anxiety, depression, insomnia, schizophrenia, psychosis and epilepsy, and also for the treatment of sleep disorders associated with journeys ("jet lag"), neurodegenerative diseases of the central nervous system such as Parkinson's disease or Alzheimer's disease, for treating cancers, or alternatively as a contraceptive or as an analgesic.

The melatoninergic analogues according to the invention are also useful for the treatment of benign hyperplasia of the prostate, skin cancers, skin complaints such as psoriasis, acne, mycosis and glaucoma, as well as for increasing the immune resistance.

They are also useful for preventing the symptoms of menopause, pre-menstrual syndromes, the effects of ageing and infant cot-death.

They are also useful in veterinary applications for controlling birth in ruminants.

The present invention thus relates also to the pharmaceutical compositions adapted for administration of the derivatives of general formula I, in particular via the oral, parenteral or rectal route, in the form of wafer capsules, tablets, gelatin capsules, drinkable solutions, injectable solutions, including delayed forms and sustained-release dressings for transdermal administration of the active principle, nasal sprays, or topical formulations (cream, emulsion, etc.), comprising a derivative of general formula I according to the invention and at least one pharmaceutically acceptable excipient.

The pharmaceutical compositions according to the invention are advantageously dosed to deliver the active principle in a single "delivery unit".

For oral administration, the effective unit doses are between 0.1 µg and 500 mg.

For intravenous administration, the effective unit doses are between 0.1 µg and 100 mg.

The melatoninergic analogues according to the invention are also useful in cosmetics, in particular for the protection of the skin against ageing, and also against hair loss.

The present invention thus relates also to a cosmetic composition comprising a derivative of general formula I according to the invention.

The cosmetic compositions according to the invention are formulated in a suitable manner, for their topical application, in particular in the form of salves, creams, emulsions, ointments, lotions, etc.

We claim:

1. Spiro (indolepyrrolidine) compounds of general formula I

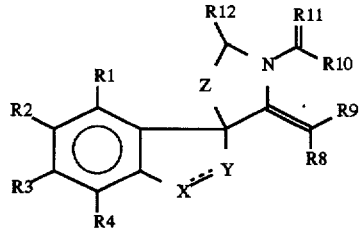

in which

—X═Y— represents a divalent group selected from

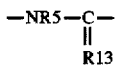 (Ib)

or

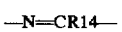 (Ic)

z represents an alkylene of formula —(CH$_2$)$_n$— with n equal to 1 or 2,

R1, R2, R3 and R4 represent, independently of each other, a hydrogen atom, a hydroxyl group or a lower alkyl, lower alkoxy, aryloxy, lower aralkoxy, halo or nitro group, R5 represents a hydrogen atom or a lower alkyl, aryl, lower aralkyl, lower alkoxy, (lower)alkylcarbonyl or perhalo (lower) alkylcarbonyl group, R6 and R7 represent, independently of each other, a hydrogen atom or a lower alkyl, aryl, lower aralkyl, lower alkoxy, (lower) alkylcarbonyl, perhalo (lower) alkylcarbonyl, (lower) alkylcarbonyloxy, perhalo (lower)alkylcarbonyloxy or halo group, R8 and R9 represent, independently of each other, a hydrogen atom or a lower alkyl, aryl or lower aralkyl group, R10 represents a hydrogen atom or a lower alkyl, aryl or lower aralkyl group, each optionally being substituted with one or more halogens, a perhalo(lower)alkyl group, an amino, (lower)alkylamino or (lower) dialkylamino group, or a lower alkoxy group, R11 represents an oxygen atom, a sulphur atom or a group N—R15, R12 represents a hydrogen atom or a lower alkyl group, R13 represents an oxygen atom, a sulphur atom, a group N—R16 or a substituted or unsubstituted methylene group, R14 represents a lower alkyl, lower alkoxy, lower alkylthio, aryl or lower aralkyl group, R15 and R16 represent, independently of each other, a hydrogen atom or a lower alkyl group, it being possible for R1–R2, R2–R3 and R3–R4 to form part of another ring, which may or may not be aromatic and may or may not have a hetero atom, it being possible for R9 and R10 together to form an alkylene group, which is optionally substituted, the racemic mixtures thereof, pure enantiomers thereof or the mixtures thereof in all proportions, and the therapeutically acceptable salts thereof, with the exception of the compounds of general formula I for which —X═Y— represents the divalent group Ic, Z represents a methylene group, R1, R3, R4, and R12 represent a hydrogen atom, R2 represents a hydrogen atom, a lower alkoxy group or a pentafluorophenylmethoxy group, R8 and R9 represent a hydrogen atom or a lower alkyl group, R10 represents a lower perhaloalkyl group and R11 represents an oxygen atom, with the exception of the compounds of general formula I for which —X═Y— represents the divalent group Ia, Z represents a methylene group, R1, R3, R4, R8, R9 and R12 represent a hydrogen atom, R2 represents a hydrogen atom or a methoxy group, R5 represents a perhalo-(lower)alkylcarbonyl group, one of R6 or R7 represents a hydrogen atom and the other represents a perhalo (lower)alkylcarbonyloxy group, R10 represents a lower perhaloalkyl group and R11 represents an oxygen atom.

2. The compound according to claim 1, wherein R11 represents an oxygen atom and R8 and R9 represents a hydrogen atom.

3. The compound according to claim 1, wherein at least one of the substituents R2 and R3 is other than a hydrogen atom.

4. The compound according to claim 1, wherein R1 and R4 represent a hydrogen atom.

5. The compound according to claim 1, wherein R12 represents a hydrogen atom and R10 is a lower alkyl group, or a perfluoromethyl, perfluoroethyl or perfluoropropyl group.

6. Compounds according to claim 1, selected from the following compounds:

5-methoxy-1,1'-N,N'-bis(perfluoroethylcarbonyl)-2-perfluoroethylcarbonyloxy-2' -methylenespiro [indoline-3,3'-pyrrolidine]

5-methoxy-1,1' -N,N'-bis(perfluoromethylcarbonyl)-2-perfluoromethylcarbonyloxy-2'-methylenespiro [indoline-3,3,-pyrrolidine]

2-oxo-5-methoxy-1'-N'-perfluoroethylcarbonyl-2'-methylenespiro [indoline-3,3,-pyrrolidine]

2-ethyl-1'-N'-methylcarbonyl-2' -methylenespiro [indoline-3,3'-pyrrolidine]

2-oxo-5-methoxy-1'-N'-perfluoromethylcarbonyl-2'-methylenespiro [indoline-3,3'-pyrrolidine]

2-oxo-5-methoxy-1'-N'-methylcarbonyl-2'- methylenespiro[indoline-3,3'-pyrrolidine]

2-oxo-5-methoxy-1'-N'-ethylcarbonyl-2'-methylenespiro [indoline-3,3'-pyrrolidine]

2-oxo-5-methoxy-1'-N'-propylcarbonyl-2'-methylenespiro[indoline-3,3'-pyrrolidine]

2-oxo-4-bromo-5-methoxy-1'-N'-perfluoroethylcarbonyl-2'-methylenespiro [indoline-3,3'-pyrrolidine]

2-oxo-5-methoxy-6-bromo-1'-N'-perfluoroethylcarbonyl-2'-methylenespiro [indoline-3,3'-pyrrolidine]

2-oxo-4-bromo-5-methoxy-1'-N'-methylcarbonyl-2'-methylenespiro [indoline-3,3'-pyrrolidine]

2-oxo-5-methoxy-6-bromo-1'-N'-methylcarbonyl-2'-methylenespiro [indoline-3,3'-pyrrolidine]

1-N-methyl-2-oxo-5-methoxy-1'-N'-perfluoroethylcarbonyl-2'-methylenespiro [indoline-3,3'-pyrrolidine]

1-N-methyl-2-oxo-5-methoxy-1'-N'-methylcarbonyl-2'-methylenespiro [indoline-3,3'-pyrrolidine]

2-oxo-1'-N'-perfluoroethylcarbonyl-2'-methylenespiro [indoline-3,3'-pyrrolidine]

2-oxo-1'-N'-methylcarbonyl-2'-methylenespiro[indoline-3,3'-pyrrolidine]

2-ethoxy-5-methoxy-1'-N'-perfluoromethylcarbonyl-2'-methylenespiro [3H-indole-3,3'-pyrrolidine]

2-ethoxy-5-methoxy-1'-N'-methylcarbonyl-2'-methylenespiro [3H-indole-3,3'-pyrrolidine]

2-ethyl-5-methoxy-1'-N'-perfluoroethylcarbonyl-2'-methylenespiro [3H-indole-3,3'-pyrrolidine]

2-ethyl-5-methoxy-1'-N'-methylcarbonyl-2'-methylenespiro [3H-indole-3,3'-pyrrolidine]

2-ethyl-1'-N'-perfluoroethylcarbonyl-2'-methylenespiro [3H-indole-3,3'-pyrrolidine]

2-ethyl-1' -N'-methylcarbonyl-2' -methylenespiro [3H-indole-3,3'-pyrrolidine].

7. The compound according to claim 3 wherein at least one of the substituents R2 and R3 is a hydroxyl or lower alkoxy group.

8. The compound according to claim 3 wherein at least one of the substituents R2 and R3 is a methoxy group.

9. The compound according to claim 5, wherein R10 is a methyl or an ethyl group.

10. The compound according to claim 5, wherein R10 is a perfluoroethyl group.

11. A pharmaceutical composition comprising a spiro (indolepyrrolidine) compound of general formula I

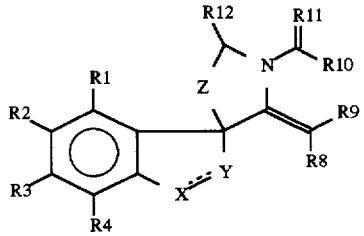

in which

—X=Y— represents a divalent group selected from

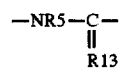   (Ib)

or

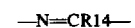   (Ic)

Z represents an alkylene of formula—$(CH_2)_n$—with n equal to 1 or 2,

R1, R2, R3 and R4 represent, independently of each other, a hydrogen atom, a hydroxyl group or a lower alkyl, lower alkoxy, aryloxy, lower aralkoxy, halo or nitro group, R5 represents a hydrogen atom or a lower alkyl, aryl, lower aralkyl, lower alkoxy, (lower)alkylcarbonyl or perhalo (lower) alkylcarbonyl group, R6 and R7 represent, independently of each other, a hydrogen atom or a lower alkyl, aryl, lower aralkyl, lower alkoxy, (lower) alkylcarbonyl, perhalo (lower) alkylcarbonyl, (lower) alkylcarbonyloxy, perhalo (lower)alkylcarbonyloxy or halo group, R8 and R9 represent, independently of each other, a hydrogen atom or a lower alkyl, aryl or lower aralkyl group, R10 represents a hydrogen atom or a lower alkyl, aryl or lower aralkyl group, each optionally being substituted with one or more halogens, a perhalo(lower)alkyl group, an amino, (lower)alkylamino or (lower) dialkylamino group, or a lower alkoxy group, R11 represents an oxygen atom, a sulphur atom or a group N—R15, R12 represents a hydrogen atom or a lower alkyl group, R13 represents an oxygen atom, a sulphur atom, a group N—R16 or a substituted or unsubstituted methylene group, R14 represents a lower alkyl, lower alkoxy, lower alkylthio, aryl or lower aralkyl group, R15 and R16 represent, independently of each other, a hydrogen atom or a lower alkyl group.

it being possible for R1–R2, R2–R3 and R3–R4 to form part of another ring, which may or may not be aromatic and may or may not contain a hetero atom, it being possible for R9 and R10 together to form an alkylene group, preferably a methylene group, which is optionally substituted, their racemic mixtures, their pure enantiomers or their mixtures in all proportions, and their therapeutically acceptable salts, and at least one pharmaceutically acceptable excipient.

12. Process for the preparation of compounds of general formula I, for which —X=Y— represents a divalent group of formula Ib and R11 represents an oxygen atom, comprising the following steps a compound of general formula IIa

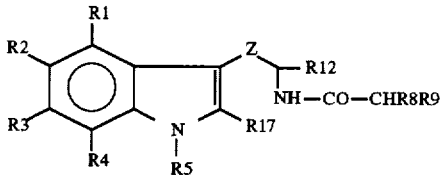

in which R1, R2, R3, R4, R5, R8, R9, R12 and Z are defined in claim 1 and R17 represents a bromine atom, is reacted with an excess of anhydride of general formula III

R20—CO—O—CO—R20    III in which R20 represents a perhalo(lower)alkyl group, and the compound of general formula IIb

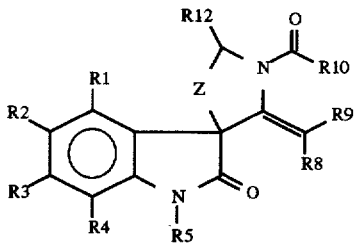

in which R1, R2, R3, R4, R5, R8, R9, R12 and Z are defined above and R10 represents a perhalo(lower)alkyl group, is obtained, followed, where appropriate, by reacting the compound of general formula I'b obtained above, with a base, in a suitable solvent, in order to obtain the intermediate of general formula IVa

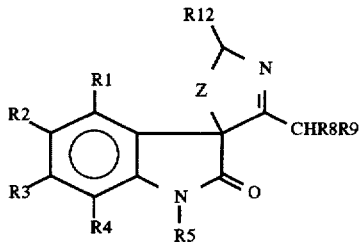

in which R1, R2, R3, R4, R5, R8, R9, R12 and Z are defined above, followed by condensation of the group R10—CO—, for which R10 is other than a perhalo(lower)alkyl group, with the free amine according to the usual techniques for the preparation of amides.

13. The process according to claim 12, wherein the base reacted with the compound of formula I'b is potassium carbonate and the suitable solvent is methanol or a methanol/water mixture.

14. The process according to claim 12, wherein the technique for the preparation of amides is selected from the group consisting of acid activation, optionally employing a coupling agent, and reaction with the corresponding anhydride of formula R10—CO—CO—R10.

* * * * *